United States Patent [19]

Anderson

[11] 4,295,856
[45] Oct. 20, 1981

[54] NITROSAMINE SPECIFICITY FOR ELECTROLYTIC CONDUCTIVITY DETECTOR

[75] Inventor: Rollen J. Anderson, Austin, Tex.
[73] Assignee: Tracor, Inc., Austin, Tex.
[21] Appl. No.: 141,900
[22] Filed: Apr. 21, 1980
[51] Int. Cl.³ ............... G01N 31/08; G01N 27/26
[52] U.S. Cl. ................ 23/232 E; 23/230 PC; 422/78; 422/89; 422/90
[58] Field of Search ........ 23/230 PC, 232 R, 232 E; 422/78, 89, 90

[56] References Cited

U.S. PATENT DOCUMENTS

| | | | |
|---|---|---|---|
| 3,877,875 | 4/1975 | Jones et al. | 23/230 PC |
| 3,973,910 | 8/1976 | Fine | 23/230 PC |
| 3,996,002 | 12/1976 | Fine | 23/232 R |
| 3,996,003 | 12/1976 | Fine et al. | 23/230 PC |
| 4,066,402 | 1/1978 | Komiyama et al. | 23/232 E |
| 4,066,411 | 1/1978 | Fine et al. | 23/230 PC |

*Primary Examiner*—Ronald Serwin
*Attorney, Agent, or Firm*—Arnold, White & Durkee

[57] ABSTRACT

N-nitrosamines in samples containing other nitrogen compounds may be selectively and quantitatively detected by use of a method and apparatus which provides for the quantitative detection of N-nitrosamines by gas chromatography, the pyrolysis of the qualitatively determined N-nitrosamines in a gold or platinum reaction environment at temperatures ranging from 500° to 700° C. and the quantitative determination of ammonia produced by the pyrolysis reaction by electrolytic conductivity detection.

29 Claims, 3 Drawing Figures

NITROSAMINE SPECIFICITY FOR ELECTROLYTIC CONDUCTIVITY DETECTOR

BACKGROUND OF THE INVENTION

This discovery relates to methods and apparatus useful for the selective and quantitative detection of N-nitrosamines in samples containing other nitrogen compounds. Specifically, this discovery relates to improved electrolytic conductivity detector systems and methods capable of selectively and quantitatively detecting N-nitrosamines.

There are several classes of nitroso derivatives but those which have become of the most significant interest are the N-nitrosamines. These are secondary amines having a nitrosyl radical connected to a nitrogen resulting in a basic N-nitrosamine configuration of ON—N=.

The interest in detecting N-nitrosamines has been stimulated by evidence which suggests these compounds may be carcinogenic to humans. At the present time, however, there exist few known methods for the quantitative detection of N-nitroso compounds.

One method which is suggested in an article entitled "Gas Chromatography and Selective Detection of N-Nitrosamines" by John W. Rhoades and Donald E. Johnson which appeared in the October, 1970 issue of Journal of Chromatographic Science, Vol. 8, page 616. In that article it is stated that the selective detection of amines and N-nitrosamines in neutral extracts of cigarette tars can be undertaken by the pyrolysis of N-nitrosamines after GC separation. The article further states that a Coulson liquid conductivity detector from Tracor, Inc. was used and that instead of hydrogenating samples in the presence of a nickel catalyst contained in a quartz tube at temperatures of about 850° C., a pyrolysis reaction was obtained by using an empty quartz tube at temperatures in the range of 400°–600° C.

It is not clear, however, whether the pyrolysis took place in the presence of hydrogen but it is specified in the article that ammonia was obtained as the degradation product of many amines and N-nitrosamines. Because of this, it would appear that the method could not be used for the accurate selective detection of N-nitrosamines.

Another method for the quantitative detection of N-nitrosamines is called the Thermal Energy Analyzer (TEA). Two articles describing testing which has been accomplished with the TEA method are:

Fine, D. H. et al, "Description of the Thermal Energy Analyzer (TEA) for Trace Determination of Volatile and Nonvolatile N-nitroso Compounds", *Analytical Chemistry*, Vol. 47, No. 7, page 1188 (1975).

Krull, I. S. et al "Thermal Energy Analysis for N-nitroso Compounds" *American Laboratory*, Vol. 11, No. 5, page 84 (May 1979).

The TEA method of nitrosamine detection involves the catalytic clevage of the nitrosyl radical from the nitroso compound. The products from the catalytic reaction are then sent through a cold trap which is designed to condense most organic materials and to allow the nitrosyl radical to move through the trap in a gaseous state. The nitrosyl radical is then directed to a stainless steel reaction chamber where it is reacted with ozone to form an electronically excited nitrogen dioxide. The light which is emitted from the nitrogen dioxide is detected by a sensitive photo multiplier and this measurement is then used to determine the quantity of N-nitroso compounds.

It appears that the TEA method can be used together with gas chromatographs or a high performance liquid chromatographs. The TEA detectors are manufactured by Thermo Electron Corporation of Waltham, Mass.

Other devices have been used for the quantitative detection of nitrogen compounds. The Hall electrolytic conductivity detector, for example, is a device which has been used as a specific detector for gas chromatography. The Hall type detector is disclosed in U.S. Pat. Nos. 4,032,296 and 3,934,193 which are incorporated herein by reference. Also, a Hall electrolytic conductivity detector has been sold by Tracor Instruments for several years.

Very basically, a Hall electrolytic conductivity detector (HECD) system includes a gas chromatograph coupled to a reactor which in turn is coupled to a differential conductivity cell. The Hall detector has three modes of operation. The first is in a halogen or chlorine detection mode. In that mode, chlorine is transformed to hydrochloric acid (HCl) and a conductivity response of ionizable HCl in a solvent-type medium is measured in the differential conductivity cell. This particular mode of operation is not pertinent to the present invention.

Another mode of operation, not pertinent to the invention, is the sulphur mode for the detection of sulfur compounds. In this mode, the sulfur is catalytically changed to $SO_2$ in the reactor. The $SO_2$ is then mixed with an electrolyte or solvent and the conductivity change in the electrolyte is measured.

The mode of detection which is most relevant to this invention is the nitrogen mode. In that mode various nitrogen compounds such as amines, carbamides, ureas, triazines and the like are reduced with nitrogen in the presence of a nickel catalyst to form quantitatively determinable amounts of ammonia. The ammonia is then mixed with a suitable solvent and the conductivity change of the solvent is measured in an electrolytic conductivity cell.

Typically, in the nitrogen mode, the HECD reactor is operated at a very high temperature of from 800 to 900 degrees C. Hydrogen as a reaction gas is fed into the nickel reaction chamber with the eluate from the chromatographic column.

The difficulty with the nitrogen mode of operation is that it is broadly applicable to a number of nitrogen compounds and therefore is not specific to nitrosamines. Any other related nitrogen compounds which might have elution times close to the desired nitrosamines will provide interfering signals which mask and prevent an effective measure of the quantitative amounts of nitrosamines present.

SUMMARY OF THE INVENTION

The instant invention provides a method and apparatus for the selective conversion of N-nitrosamines, in a sample containing other nitrogen compounds, to ammonia in a non-catalytic, reductive environment of gold or platinum and free from nickel at temperatures ranging from about 500 to about 700 degrees C. The method is particularly adapted for the selective and quantitative detection of N-nitrosamines. The apparatus of the instant invention is basically an improvement of an electrolytic conductivity detector which permits the apparatus to selectively and quantitatively detect N-nitrosamines.

In the method, N-nitrosamines in samples containing nitrogen compounds may be qualitatively determined by chromatographic means, such as by gas chromatography. The eluate from the chromatographic column, designed for the qualitative detection of N-nitrosamine, may be pyrolyzed to produce ammonia in a noncatalytic environment of gold or platinum and free from nickel in the presence of hydrogen, at temperature ranges between about 500 and 700 degrees C. The products from the pyrolysis reaction should be scrubbed with a suitable scrubber to remove the acid components. Then, the quantity of ammonia produced by pyrolysis can then be measured by electrolytic conductivity detection.

In qualitatively detecting N-nitrosamines by gas chromatography, the carrier gas used in the elution process should be one which contains no reducible nitrogens. Such nitrogens might interfere in the subsequent quantitative measurement of N-nitrosamines unless they were somehow removed from the system before the eluate was pyrolyzed. Because of this, noble gases such as helium or argon should be used as carrier gases.

The apparatus of the instant invention is basically a modification of an electrolytic conductivity detector of the type capable of reducing nitrogen compounds to ammonia in a reaction zone. The ammonia thus produced can then be quantitatively measured by electrolytic conductivity means. The electrolytic conductivity detector may be modified by providing it with a reaction zone having a metallic surface of gold or platinum. The reaction zone should have some means of heating it to maintain the zone at a temperature ranging from 500 to about 700 degrees C. Also, the reaction zone must be substantially free from nickel since at elevated temperatures in a reductive environment nitrogen compounds other than N-nitrosamines will be catalytically converted to ammonia.

In operation, the reaction surface having a metallic surface of gold can be maintained at the higher end of the temperature range, about 550 to about 700 degrees C., in order to pyrolytically reduce N-nitrosamines to ammonia. Where the metallic surface is platinum, the reaction zone can be maintained at the lower end of the scale, that is, from about 500 to about 600 degrees C.

BRIEF DESCRIPTION OF THE DRAWINGS

The accompanying drawings illustrate the preferred embodiment of the invention, and in which.

DESCRIPTION OF THE PREFERRED EMBODIMENT

Figure 1:
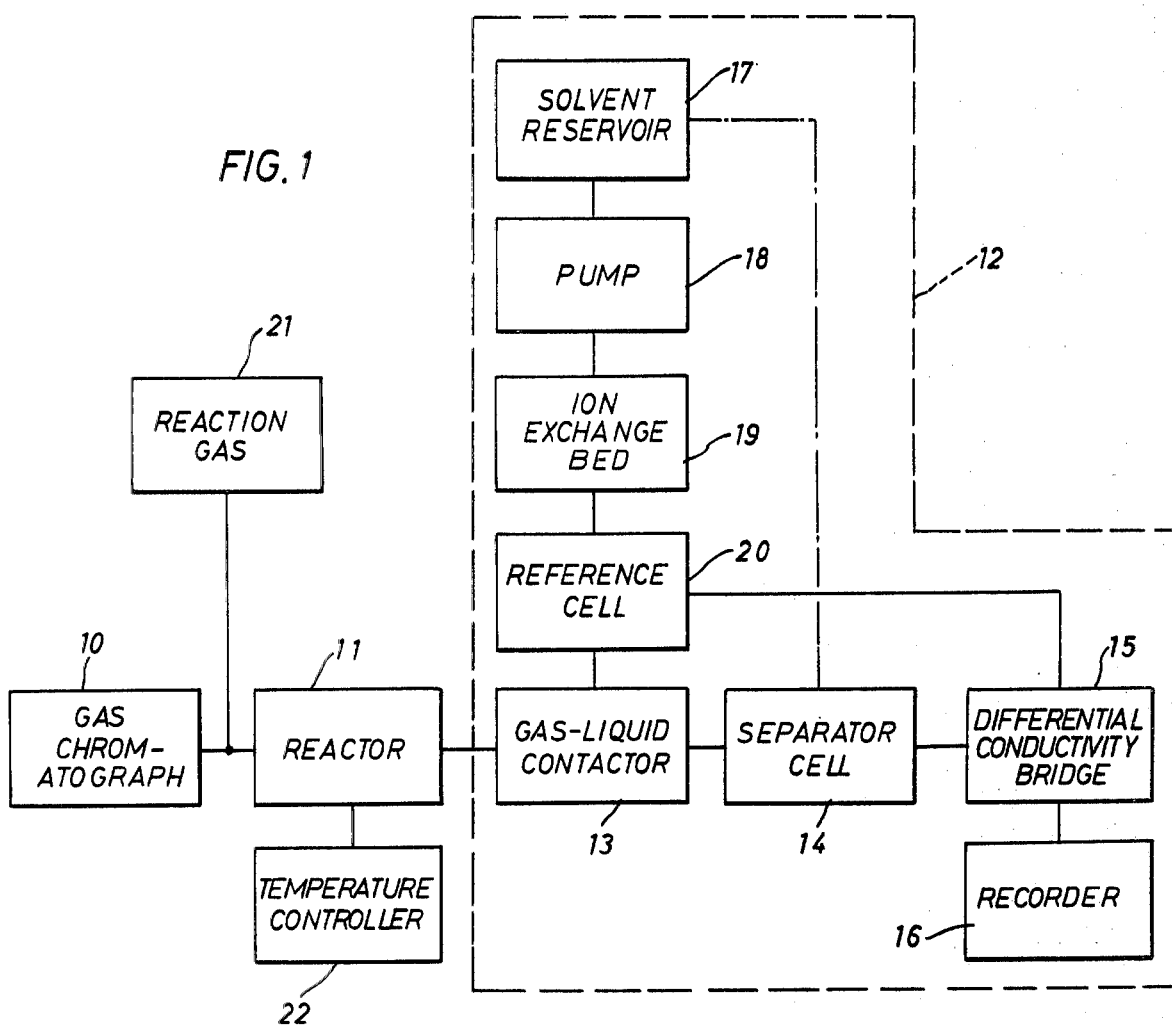
FIG. 1 is a block diagram of an electroconductivity detection system of this invention.

As shown in the block diagram of FIG. 1, the preferred embodiment of the instant invention may include a gas chromatograph 10 in communication with a reactor 11. The reactor in turn is connected to a differential conductivity cell and accessories which are collectively referred to as 12 in FIG. 1. The differential conductivity cell and accessories include a gas-liquid contactor 13, a separator cell 14, a differential conductivity bridge 15 with a recorder 16, a solvent reservoir 17 a solvent metering pump 18, an ion exchange bed 19, and a reference cell 20. Also shown in FIG. 1 are a reaction gas supply 21 and a temperature controller 22 for control of the reactor temperature.

In the type of detection system illustrated in FIG. 1 a sample containing N-nitrosamines and other nitrogen compounds is eluted through a column in the gas chromatograph 10, which column is designed for the qualitative detection of N-nitrosamines. As is known, the column can be calibrated in order to qualitatively determine the presence of N-nitrosamines in the sample. The sample should be passed through the column with a carrier gas which has no reducible nitrogens, such as an inert gas like helium or argon.

The eluate from the column can then be introduced into reactor 11 with hydrogen from reaction gas supply 21. The reactor has a temperature controller 22 which maintains a reaction zone at a temperature ranging from 500 to 700 degrees C. The inner surface of the reaction zone is either gold or platinum. In the reaction zone the N-nitrosamines are pyrolytically reduced to ammonia.

The ammonia produced in the reactor is then processed in the differential conductivity cell 12. Before processing, the products from pyrolysis should be scrubbed with a suitable resin such as a quartz thread containing potassium hydroxide. A suitable solvent which will dissolve the ammonia is pumped from the solvent reservoir 17 by a solvent metering pump 18 through ion exchange bed 19 and into gas liquid contactor 13 where it is mixed with the ammonia from the reactor. The gas liquid mixture formed in the contactor 13 is separated into gas and liquid phases in the separator cell 14. The conductivity of the liquid is then measured. The conductivity of this liquid and the conductivity of the solvent alone can be compared to determine the quantity of ammonia present and thus, the quantity of N-nitrosamines in the sample.

Figure 2:
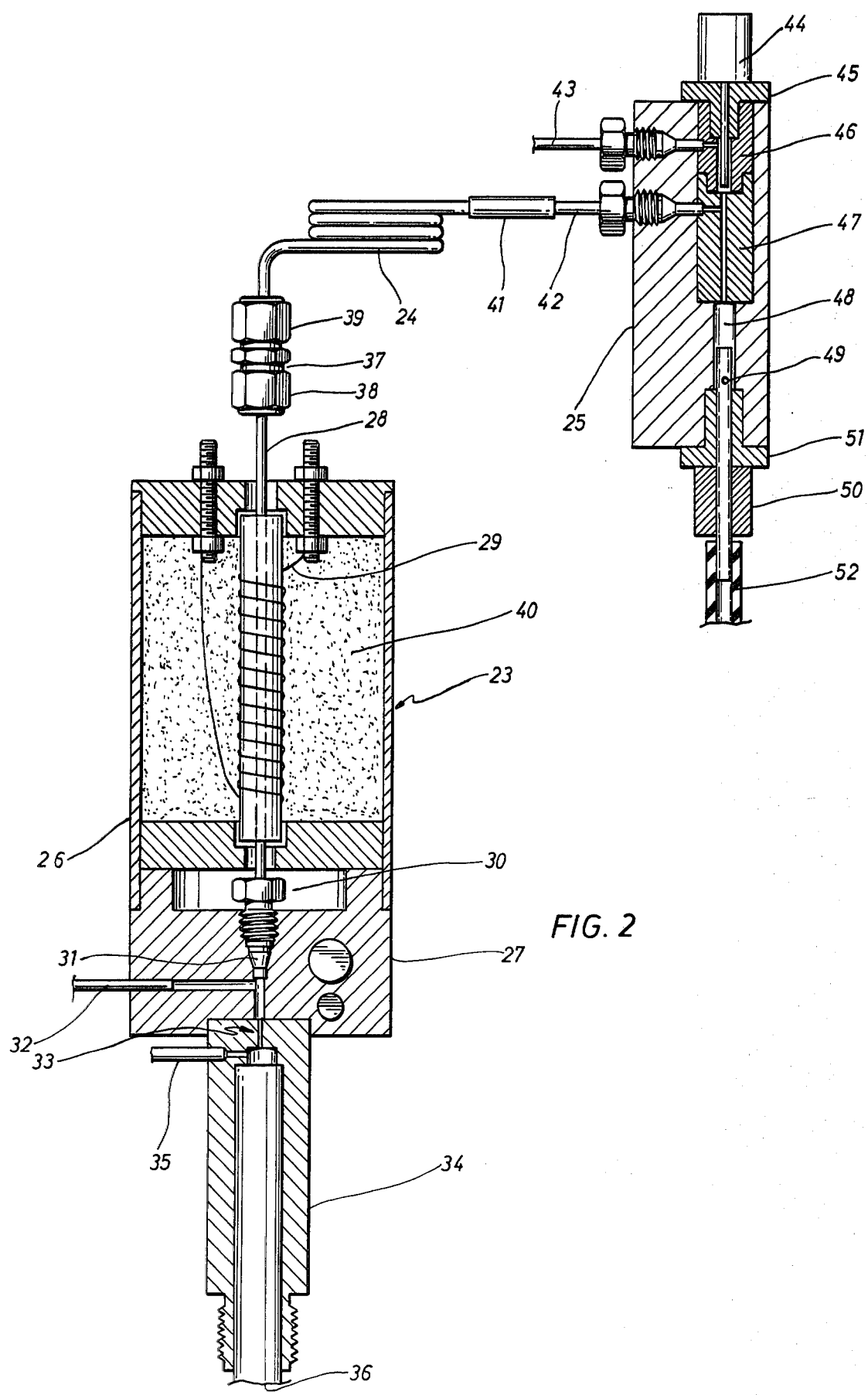
FIG. 2 is a cut-away side view of a reactor and a conductivity cell connected and operated in accordance with the preferred embodiment of this invention.

Reference should now be had to FIG. 2 which is a cutaway side view of a combination of a reactor and a conductivity cell used in the preferred embodiment of the instant invention. This preferred embodiment of the instant invention is currently available from Tracor Instruments of Austin, Tex. and is designated at 700 A Hall electrolytic conductivity detector. The system can be coupled to a gas chromatograph and as such is available as a Tracor 560/700 A Gas Chromatograph with an Electrolytic Conductivity Detector.

Shown in FIG. 2 is a reactor assembly 23 which is connected through a scrubber 24 to a differential conductivity cell 25.

The reactor assembly includes a housing 26, a base 27 and a reaction tube 28 surrounding by a heating element 29. The heating element should preferably be a platinum wire and, although not shown, it should be apparent that a thermocouple feedback system can be employed to maintain the temperature of the reactor. The reaction tube may be a metal tube about 3.75 inches long, 1/16 inch OD and 0.03 inch ID. The inside surface of the reaction tube may be either gold or platinum. If the interior surface is plated with gold or platinum there is a likelihood that the metal could migrate and expose a surface which might cause an undesirable catalytic reduction of nitrogen compounds other than N-nitrosamine to ammonia. For that reason, it is preferred to utilize a solid gold or a solid platinum tube as the reaction tube. The reaction tube should be insulated from the reaction housing by any suitable insulation 40.

The reaction tube is connected to the reactor base by a 1/16 inch tube nut 30 and a brass or stainless steel ferrule 31. The reactor base has a bore 32 to permit the entry of a suitable reaction gas such as hydrogen into the reactor. The reactor base has another bore 33 which meets in a T configuration with the reaction gas bore. The eluate from the chromatographic column is introduced through that bore. Attached to the reactor base is an assembly 34 for connection with the gas chromatograph. The assembly includes a vent 35, which can be utilized to bleed undesirable deposits from the reactor system, and an eluate inlet which can be connected to the GC column. The upper side of the reaction tube 28 can be connected by any suitable means to a scrubber 24. For example, the ferrule 37 can include a back ferrule 38 having an inner graphite ferrule (not shown) and stainless steel back 39 having an inner stainless steel back ferrule 40 (not shown).

Scrubber 24 is utilized to remove acidic compounds such as hydrogen sulfide and other acidic components which may be produced in the reductive environment of the reactor. The scrubber should desirably contain a quartz thread containing potassium hydroxide. In order to remove acid gases from the electrolyte a scrubber having 33 weight percent of Rohm & Haas IRN-150 resin and 67 weight percent of Rohm & Haas IRN-78 resin should preferably be utilized.

The scrubber is connected to heat shrink Teflon tubing 41 and Teflon gas inlet tube 42 which can be attached to electroconductivity cell 25 by a suitable nut and ferrule arrangement as shown. Also connected to the differential conductivity cell block 25 is a solvent inlet 43 through which solvent can be introduced into the cell. The cell 25 also has a top electrode 44 insulated from the cell by insulator 45. The cell 25 also includes an outer electrode 46, a gas liquid contactor 47, gas liquid separator 48, solvent exit hole 49, bottom electrode 50 insulated from cell block 25 by insulator 51 and an exit line 52. The differential conductivity cell 25 may be made of any suitable material but it is preferred to use high density plastic material such as Vespel or Kel-F. Other components of the cell can be made of stainless steel.

In the operation of the electrolytic conductivity cell the solvent enters through inlet 43 and flows through the reference conductivity cell which is formed by the top electrode 44 and the outer electrode 46. The solvent then flows into gas liquid contactor 47 where it is mixed with the incoming gas from the scrubber 24. The gas liquid mixture formed in the contactor 47 is separated into gas and liquid phases in the separator 48. The gas then exits the exit line 52. The liquid phase flows between the outer wall of the bottom electrode 50 and the inner wall of the gas liquid separator 48. The space between these surfaces constitutes the space in which the conductivity of the liquid is measured. The liquid then exits the bottom electrode through a solvent exit hole 49. The gas and liquid phases are then recombined and returned to the solvent reservoir. It should be apparent that the top electrode is insulated from the gas liquid separator 48 such that no electrical conduit is formed between the top electrode 44 via gas liquid separator 48 and the liquid phase and the bottom electrode 50.

The solvent used should preferably be a 50%-propanol-water mixture. It is important that the solvent have a basic pH characteristic. Otherwise, if acidic, a neutralization reaction would occur between the ammonia and the solvent. The water and propanol mixture should be ion exchanged over a suitable basic ion exchange resin which will provide a basic characteristic to the solvent to insure its nonacidic character.

Figure 3:
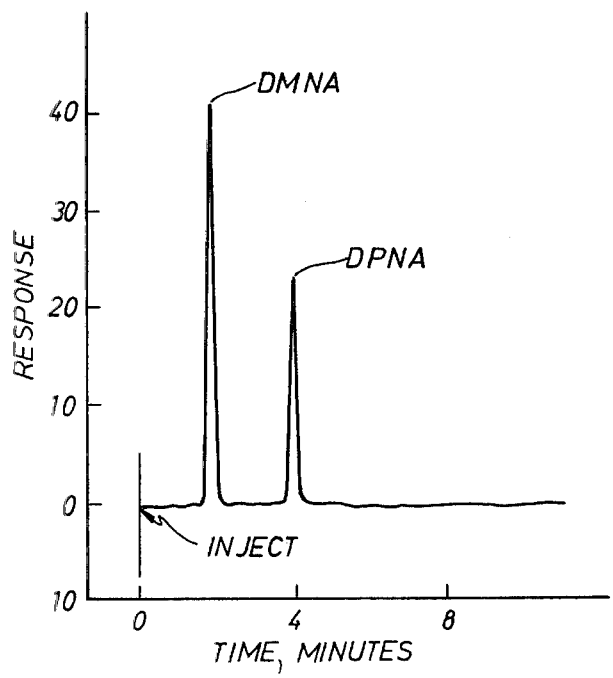
FIG. 3 is an illustration of a standard chromatogram obtainable with a Tracor 560/700 A Electroconductivity Detector in the nitrosamine mode.

Referring now to FIG. 3 there is illustrated the response to a standard sample of a mixture of one nanogram per microliter of dimethyl nitrosamine (DMNA) and one nanogram per microliter of dipropyl nitrosamine (DPNA) obtained with a Tracor 560/700 A Hall Electrocond Detector of the type contemplated by this invention. Preferably the response as illustrated in FIG. 3 should be about 30% of full scale for DMNA and 20% for DPNA. Of course, range and attenuation values may be suitably set to obtain desired responses when analyzing a sample containing an unknown quantity of N-nitrosamines.

In qualitatively determining the presence of nitrosamines as illustrated in FIG. 3 a Tracor nitrosamine 8 foot by 2 millimeter I.D. glass columns should be utilized. The carrier gas flow rate should be set at 25 ml/min. and a 2 microliter sample should be injected into the column which should be maintained at 145° C. The reactor should be maintained at a temperature of 700° C. during the pyrolysis reaction.

In operating the Tracor 560/700 A system, pure hydrogen should be used as the reaction gas and helium as the carrier gas. The flow of these gases should be regulated with metal regulators having metal diaphragms and stainless steel or nickel gas lines should be used to connect the source of these gases to the instrument.

The description of the preferred embodiment is not intended to limit the scope of this invention. Various modifications of the disclosed embodiments, as well as other embodiments of the invention, may be apparent to persons skilled in the art upon reference to this description. It is therefore contemplated that the appended claims will cover any such modifications or embodiments as fall within the true scope of the invention.

What is claimed is:

1. A method for selectively pyrolyzing N-nitrosamines to ammonia from a sample containing other nitrogen compounds, which comprises:
   contacting said sample with hydrogen at a temperature ranging from about 500° to about 700° C., in a non-catalytic environment, which environment is free of nickel and is a reactor having a metallic surface exposed to said sample during pyrolysis wherein said metal surface is gold or platinum.

2. The method of claim 1 wherein said metallic surface is gold and said temperature ranges from about 550° to about 700° C.

3. The method of claim 1 wherein said metallic surface is platinum and said temperature ranges from about 500° to about 600° C.

4. A method for selectively and quantitatively analyzing for N-nitrosamines in the eluate of a chromatographic column, said eluate containing other nitrogen compounds, which comprises:
   pyrolyzing said eluate in the presence of hydrogen to produce ammonia at a temperature ranging from about 500° to about 700° C., in a non-catalytic environment, which environment is free of nickel and is a reactor having a metallic surface exposed to said eluate during said pyrolysis wherein said metal surface is gold or platinum; and
   determining the quantity of said ammonia produced by electrolytic conductivity measurement.

5. The method of claim 4 wherein said metallic surface is gold and said temperature ranges from about 550° to about 700° C.

6. The method of claim 4 wherein said metallic surface is platinum and said temperature ranges from about 500° to about 600° C.

7. A chromatographic and electrolytic conductivity detection method of selectively and quantitatively analyzing for N-nitrosamines from samples containing other nitrogen compounds which comprises:
eluting said sample with a carrier gas free from reducible nitrogen through a chromatographic column designed for the qualitative detection of N-nitrosamines;
pyrolyzing the eluate from said column in the presence of hydrogen to produce ammonia at a temperature ranging from about 500° to about 700° C. in a non-catalytic environment which environment is free from nickel and is a reactor having a metallic surface exposed to said sample during said pyrolysis wherein said metal surface is gold and platinum; and
determining the quantity of said ammonia produced by electrolytic conductivity measurement.

8. The method of claim 7 wherein said carrier gas is a noble gas.

9. The method of claim 8 wherein said carrier gas is helium.

10. The method of claim 7 wherein said metallic surface is gold and said temperature ranges from about 550° to 700° C.

11. The method of claim 7 wherein said metallic surface is platinum and said temperature ranges from about 500° to about 600° C.

12. An apparatus for the quantitative detection of N-nitrosamines in samples containing other nitrogen components which comprises:
a reactor assembly comprising:
a reaction zone having an interior metallic surface of gold or platinum;
means for maintaining said reaction zone at a temperature of between about 500° and 700° C.;
means for introducing hydrogen gas into said reaction zone;
means for introducing said sample into said reaction zone;
means for removing products including ammonia from said reaction zone; and
an electrolytic conductivity detector communicating with said reactor assembly for determining the quantity of ammonia produced in said reactor assembly.

13. The apparatus of claim 12 wherein said reaction zone is defined by the interior surface of a tube.

14. The apparatus of claim 13 wherein said metal is gold.

15. The apparatus of claim 14 wherein said reaction zone is a solid gold tube.

16. The apparatus of claim 13 wherein said metal is platinum.

17. The apparatus of claim 16 wherein said reaction zone is a solid platinum tube.

18. In an electrolytic conductivity detector of the type capable of reducing nitrogen compounds to ammonia in a reaction zone, the amount of ammonia of which is quantitatively measurable by conductivity, the improvement rendering said detector capable of selectively and quantitatively detecting N-nitrosamines from a sample containing other nitrogen compounds, which comprises a reaction zone having a metallic surface of gold or platinum.

19. The apparatus of claim 18 wherein said reaction zone is defined by the interior surface of a tube.

20. The apparatus of claim 19 wherein said metallic surface is gold.

21. The apparatus of claim 20 wherein said improvement consists essentially of a solid gold tube.

22. The apparatus of claim 19 wherein said metallic surface is platinum.

23. The apparatus of claim 22 wherein said improvement consists essentially of a solid platinum tube.

24. A chromatographic and electroconductivity detection system for selectively and quantitatively analyzing for N-nitrosamines from a sample containing other nitrogen compounds which comprises:
chromatographic means for qualitatively detecting for N-nitrosamines;
a reactor assembly, communicating with said chromatographic means, comprising:
a reaction zone having a metallic interior metallic surface of gold or platinum; and
means for maintaining said reaction zone at a temperature of between about 500° and 700° C.; and
an electrolytic conductivity detector communicating with said reactor assembly for determining the quantity of ammonia produced in said reaction zone.

25. The system of claim 24 wherein said reactor assembly further comprises:
means for introducing hydrogen gas into said reaction zone;
means for introducing the eluate from said chromatographic means into said reaction zone; and
means for removing reactants including ammonia from said reaction zone.

26. The system of claim 25 wherein said chromatographic means comprises:
a column designed for the qualitative detection of N-nitrosamines; and
a source of carrier gas containing no reducible nitrogens for carrying said sample through said column.

27. The system of claim 26 wherein said reaction zone is defined by the interior surface of a tube.

28. The system of claim 27 where said reaction zone consists essentially of a solid gold tube.

29. The system of claim 27 wherein said reaction zone consists essentially of a solid platinum tube.

* * * * *